(12) United States Patent
Grust et al.

(10) Patent No.: US 7,779,020 B2
(45) Date of Patent: Aug. 17, 2010

(54) SMALL-FOOTPRINT APPLICATIVE QUERY INTERPRETER METHOD, SYSTEM AND PROGRAM PRODUCT

(75) Inventors: Torsten Grust, Constance (DE); Jonas S. Karlsson, San Francisco, CA (US)

(73) Assignee: International Business Machines Corporation, Armonk, NY (US)

( * ) Notice: Subject to any disclaimer, the term of this patent is extended or adjusted under 35 U.S.C. 154(b) by 822 days.

(21) Appl. No.: 10/090,068

(22) Filed: Mar. 1, 2002

(65) Prior Publication Data
US 2003/0167261 A1 Sep. 4, 2003

(51) Int. Cl.
G06F 7/00 (2006.01)
(52) U.S. Cl. ...................................... 707/760
(58) Field of Classification Search ............... 707/4, 707/3, 103 Y; 717/106
See application file for complete search history.

(56) References Cited

U.S. PATENT DOCUMENTS

| | | | | |
|---|---|---|---|---|
| 4,916,610 | A | 4/1990 | Bapat | 364/300 |
| 5,063,133 | A | 11/1991 | Kubo et al. | 430/122 |
| 5,504,885 | A * | 4/1996 | Alashqur | 717/141 |
| 5,701,400 | A | 12/1997 | Amado | 395/76 |
| 5,761,494 | A | 6/1998 | Smedley et al. | 395/604 |
| 5,806,060 | A | 9/1998 | Borgida et al. | 707/3 |
| 5,826,077 | A * | 10/1998 | Blakeley et al. | 707/4 |
| 5,826,258 | A | 10/1998 | Gupta et al. | 707/4 |
| 5,850,550 | A * | 12/1998 | Li et al. | 717/154 |
| 5,860,010 | A | 1/1999 | Attal | 395/706 |
| 5,862,383 | A * | 1/1999 | Laitinen | 717/109 |
| 5,864,840 | A * | 1/1999 | Leung et al. | 707/2 |
| 5,974,253 | A | 10/1999 | Nahaboo et al. | 395/701 |
| 5,987,455 | A * | 11/1999 | Cochrane et al. | 707/4 |
| 5,995,958 | A * | 11/1999 | Xu | 707/3 |
| 6,063,133 | A | 5/2000 | Li et al. | 717/9 |

(Continued)

FOREIGN PATENT DOCUMENTS

EP 0251594 A2 6/1987

(Continued)

OTHER PUBLICATIONS

The CORAL Deductive system, VLDB Journal 2, 161-210, Raghu Ramakrishnan et al.*

(Continued)

*Primary Examiner*—Etienne P LeRoux
*Assistant Examiner*—Cindy Nguyen
(74) *Attorney, Agent, or Firm*—Hovey Williams LLP (57) ABSTRACT

A method system, and program product for managing a relational database in a pervasive computing environment. The system receives queries in a query language, and represents the queries in accordance with a declarative language paradigm, this may be explicit or implicit. The queries represented in a declarative language paradigm are converted (e.g., represented, translated, or cross-compiled) to an imperative language (including a data structure that is interpreted by an imperative language); and the imperative language queries are executed on the database. The queries may be explicitly converted to an intermediate declarative representative, and thereafter converted to an imperative language representation of the original queries for execution. Alternatively, the queries may be directly converted to an imperative language representation of the declarative language and the imperative language queries executed on the database.

6 Claims, 4 Drawing Sheets

U.S. PATENT DOCUMENTS

| | | | |
|---|---|---|---|
| 6,094,528 | A | 7/2000 | Jordan .................... 395/704 |
| 6,182,062 | B1 | 1/2001 | Fujisawa et al. ............. 707/3 |
| 6,243,703 | B1 | 6/2001 | Couch et al. ................ 707/10 |
| 6,336,029 | B1 | 1/2002 | Ho et al. .................. 434/362 |
| 6,378,126 | B2 * | 4/2002 | Tang ....................... 717/143 |
| 6,438,608 | B2 * | 8/2002 | Biliris et al. ............. 709/245 |
| 6,457,172 | B1 * | 9/2002 | Carmichael et al. .......... 717/141 |
| 6,496,833 | B1 * | 12/2002 | Goldberg et al. ............ 707/102 |
| 6,581,205 | B1 * | 6/2003 | Cochrane et al. ............ 717/140 |
| 6,711,672 | B1 * | 3/2004 | Agesen ..................... 712/227 |
| 6,901,428 | B1 * | 5/2005 | Frazier et al. ............. 709/203 |
| 6,938,041 | B1 * | 8/2005 | Brandow et al. ............. 707/10 |
| 7,027,975 | B1 * | 4/2006 | Pazandak et al. ............ 704/9 |
| 2001/0056420 | A1 * | 12/2001 | Steele et al. .............. 707/8 |
| 2002/0188616 | A1 * | 12/2002 | Chinnici et al. ............ 707/102 |
| 2003/0055820 | A1 * | 3/2003 | Aigen ...................... 707/4 |
| 2003/0110478 | A1 * | 6/2003 | Duesterwald et al. ......... 717/137 |
| 2004/0015834 | A1 * | 1/2004 | Mestre et al. .............. 717/106 |

FOREIGN PATENT DOCUMENTS

| | | | |
|---|---|---|---|
| EP | 1126384 | A2 | 10/1993 |
| JP | 10269119 | A2 | 10/1998 |

OTHER PUBLICATIONS

Simon Peyton Jones et al. "Bridging the gulf: a common intermediate language for ML and Haskell", Copyright 1998 ACM.*

Alan S. Gunderson "An SQL Interface for Common LISP", Digital Equipment Corporation, copyright 1991.*

Plate et al. "Optimizations Enabled by a relational data model view to querying data streams", copyright 2001 IEEE.*

"Bridging the gulf: a common intermediate language for ML and Haskell", Copyright 1998 ACM.*

"Using JDeveloper to Build Oracle XML Applications". Copyright 199-2001, Oracle Corporation.*

Oracle8i SQLJ Developer's Guide and Reference Release 8.1.5 A64684-01 Copyright 1999.*

Rasmus, D. W., "Legacy Knowledge Based System", Object Magazine (USA), vol. 7, No. 10, Dec. 1997, p. 27-8.

Gluche et al., "Incremental Updates for Materialized OQL Views", University of Konstanz, Department of Mathematics and Computer Science, D-78457 Konstanz, Germany.

Grust, et al., "How to Comprehend Queries Functionally", Journal of Intelligent Information Systems 12. 191-218 (1999).

Grust, T., "Comprehending Queries", PhD Dissertation., Department of Mathematics and Computer Science, University of Konstanz. D-78457 Konstanz, Germany, 1999.

* cited by examiner

FIG. 6
SELECT x, b FROM S, T WHERE y = a

FIG. 7
SELECT x, b FROM S, T WHERE y > a

FIG. 8
SELECT * FROM S ORDER BY x

FIG. 9
SELECT SUM (y), COUNT(*), FROM S

FIG. 10
SELECT (SELECT (SUM A)) FROM t WHERE a > 1) FROM S

FIG. 11
SELECT COUNT (z), x,y FROM S, GROUP BY x,y

FIG. 12
SELECT x + y FROM S

FIG. 13
SELECT y - z FROM S

SMALL-FOOTPRINT APPLICATIVE QUERY INTERPRETER METHOD, SYSTEM AND PROGRAM PRODUCT

FIELD OF THE INVENTION

The invention relates to database management methods and to database management systems. The methods and systems are used for searching a database in a computer system, including sequential searching, primary and secondary index searching. The method and system further relate to translating an external access to a database or database files into an internal access to the database or files, and translation of an external query format into an intermediate or internal query format by converting program code from one form to another.

BACKGROUND OF THE INVENTION

1. Pervasive Computing

"Pervasive computing" is the synergistic product of personal digital assistants (PDA's) and other handheld devices with portable communications. IBM CEO Lou Gerstner has described "pervasive computing" as "a billion people interacting with a million e-businesses through a trillion interconnecting intelligent devices" His vision is fast becoming reality, as "pervasive computing" computerizes everything from refrigerators to thermostats to a palm based data mining entry point or even a handheld concierge.

Pervasive computing involves the same kind and degree of paradigm shift and the same fundamental breakthrough in user experience that the shift from text based systems to graphical user interfaces brought to personal computing, and that the browser brought to the Internet. For example, neither PDA's nor portable telephones were widely used until they became more user-friendly and more capable. However, as both portable telephones and PDA's became both more capable and more user friendly, a natural convergence developed. This convergence, led to wireless application protocols and wireless markup languages, and gave rise to "pervasive computing."

Figure 1:
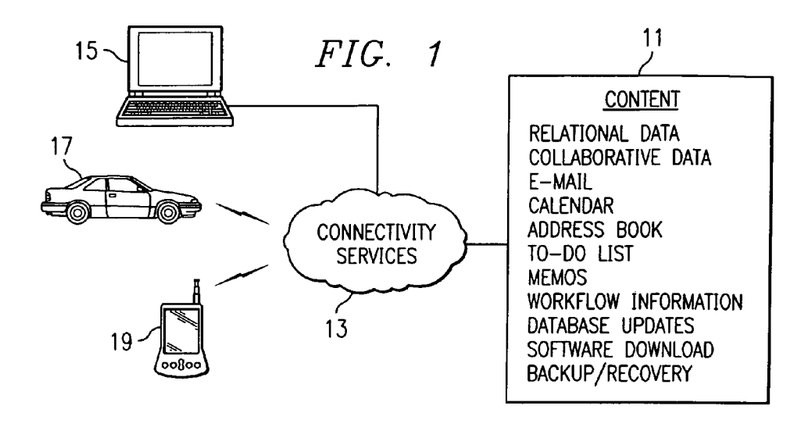
FIG. 1 illustrates the pervasive computing environment of the invention, where content, illustrated in the FIGURE as relational data, collaborative data, e-mail, address book data, to-do list, memos, work flow information, database updates, software downloads, and user backup and recover are resident on one or more servers. The one or more servers are connected through connectivity services, to various clients, including personal computers, mobile computers, and hand held devices.

"Pervasive Computing" is about connecting a wide variety of client devices (such as PDA's cellular phones, automotive computers, home gateways, and traditional PC's) to a modern Web environment, and enabling interaction and e-business to occur via technology that is virtually invisible to the end user. As shown in FIG. 1, pervasive computing enables a broad range of end user devices, such as a laptop computer 101, an automotive computer 103, and a cellular telephone having computing capability, 105, to communicate through connectivity services, 111, various servers providing content 121. One enabling element of "pervasive computing" is connectivity, which includes gateways and proxies, between end user devices and servers.

Figure 2:
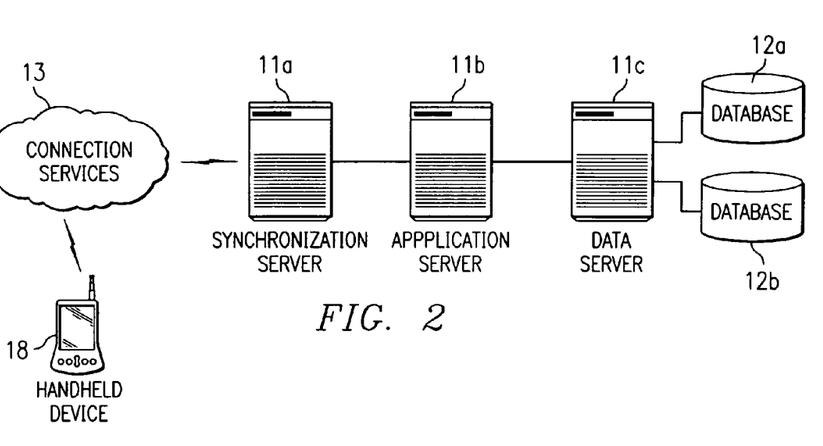
FIG. 2 illustrates another aspect of the pervasive computing environment of the invention, here a handheld device is connected through connection services and a series of servers to databases. The servers include synchronization servers, application servers, and data servers.

Another element of "pervasive computing", illustrated in FIG. 2, is the synchronization server, 201, connecting a client, here a handheld device, 109, through connectivity services, 111, to an application server 221, a data server, 231, and databases, 241, 243. The synchronization server is a program that manages the data synchronization between the client and the server.

One challenge facing "pervasive computing" developers is how to port PC and network centric applications to handheld devices. In this regard, "pervasive computing" integrates portable and handheld, especially wireless, devices into a single, transparent environment, with network centric devices and client-server and web based applications. Exemplary are Microsoft Windows CE equipped devices and Palm Computing Palm OS equipped devices. However, porting network and PC and server based applications to portable, handheld, and wireless devices presents challenges. These challenges arise from the small memory size and limited processing power of the devices. These challenges will be illustrated with respect to Microsoft Windows CE and Palm Computing Palm OS platforms.

2. Microsoft Windows CE

Windows CE is a 32 bit operating system with features like multitasking and multithreading. It is also a highly customizable OS, in the sense that it can be altered to suit the needs of a specific hardware platform.

Memory plays a vital role in application development in the Windows CE environment. While desktop PC developers generally need not worry about memory constraints because of the huge memory capacity of the current day desktop PCs. This is not the case with Windows CE devices. Windows CE devices in general will have much less RAM than a desktop PC. Moreover they do not have disk drives or other mass storage devices.

Windows CE devices have a RAM and a ROM. ROM holds the permanent information, which includes the actual OS and other applications like Pocket Word, Pocket Excel, etc that come integrated with the OS and the device. RAM has two further divisions called the Program Memory and Storage Memory (Object Store). Program memory is primarily used for the execution of applications; it generally stores the heaps and stacks of an application. Program memory could be compared with the RAM found in desktop PCs where all applications are generally loaded for execution. A very significant difference between ROM resident Windows CE applications and PC applications is that ROM based applications are executed in place without being loaded into the RAM section (Program Memory) thereby saving limited RAM space and at the same time accelerating the execution speed. Storage Memory is equivalent to the RAM disk (also known as RAM drive) which is generally used as a simulated hard disk. The storage memory or the Object store is the placeholder for the Windows CE file system, Registry and the Databases. All these objects have their respective APIs for accessing them. All of these APIs are almost complete except for the absence of few features. These include the lack of functions that directly reference volumes (directories) in the case of file system, the lack of security attributes with functions corresponding to the Registry and the lack of many features found in the modern day databases. The database API is unique to Windows CE and is primarily used for storing simple data like address lists or mail folders. All the applications are generally stored in the object store and loaded into program memory during execution.

3. Palm Computing Palm OS

The Palm Computing platform device is also designed differently than a desktop computer, and users simply interact with the device differently than they do desktop computers.

The Palm Computing platform device does not have the same processing power as a desktop PC. It is intended as a satellite viewer for corresponding desktop applications. For this reason, if an application needs to perform a computationally intensive task, the developer should implement that task in the desktop or network application instead of the device application.

A further challenge to the developer is the limited memory of a Palm OS device. The Palm OS device has limited heap space and storage space. Different versions of the device have upwards of 512 K to 8 MB or more total of dynamic memory and storage available. Earlier Palm OS devices did not have a disk drive or PCMCIA support. Because of the limited space and power, optimization is critical, especially optimization of heap space, speed, and code size.

Additionally, because of the limited storage space, and to make synchronization with the desktop computer more efficient, Palm OS does not use a traditional file system. Data is stored in memory chunks called Palm records, which are grouped into Palm databases. A Palm database is analogous to a file. The difference is that data is broken down into multiple Palm records instead of being stored in one contiguous chunk. To save space, a user edits a database in place in memory instead of creating it in RAM and then writing it out to storage.

Palm OS applications are generally single-threaded, event-driven programs. Only one program runs at a time.

Each application has a PilotMain function that is equivalent to main in C programs. To launch an application, the system calls PilotMain and sends it a launch code. The launch code may specify that the application is to become active and display its user interface (called a normal launch), or it may specify that the application should simply perform a small task and exit without displaying its user interface. The sole purpose of the PilotMain function is to receive launch codes and respond to them.

Palm OS is an event-based operating system, so Palm OS applications contain an event loop; however, this event loop is only started in response to the normal launch. A Palm OS application may perform work outside the event loop in response to other launch codes.

A developer implements a Palm OS application's features by calling Palm OS functions. Palm OS consists of several managers, which are groups of functions that work together to implement a feature. As a rule, all functions that belong to one manager use the same prefix and work together to implement a certain aspect of functionality. Managers are available to, for example, generate sounds, send alarms, perform network communication, and beam information through an infrared port.

4. The Challenge of Handheld and Portable Devices

Handheld and portable devices present special challenges, especially storage space and processing power challenges, to the developer seeking to create or port existing applications to these platforms, while maintaining end user transparency with network and desktop applications. Specifically, a need exists for a programming paradigm, a program product, a method of utilizing the program product, and a device incorporating the program product so as to provide transparency and compatibility between a handheld device and a desktop or network device.

SUMMARY OF THE INVENTION

The method, portable device, system, and program product described herein provide transparency and compatibility between a small memory device, exemplified by a handheld device, especially one of limited processing power, and a desktop or network application, device, or system. This is accomplished through a functional program in which SQL commands are initially interpreted, translated, or compiled as functional language functions (for example ML, LISP or HASKELL functions), which are in turn interpreted, translated, or compiled into a high level imperative language (including converting the queries to a data structure that is interpreted or capable of being interpreted by an imperative language), where interpretive languages are exemplified by such languages as C, C++, Java, Cobol, ADA, and the like, and including preferably object oriented imperative languages, such as C++, Java, Smalltalk, or Modula2.

Our invention resides in a method system, and program product for managing a relational database in a pervasive computing environment. The system receives queries in a query language, and represents the queries in accordance with a declarative language paradigm, this may be explicit or implicit. The queries represented in a declarative language paradigm are converted to an imperative language (or to a data structure that can be interpreted by an imperative language); and the imperative language queries are executed on the database. The queries may be explicitly converted to an intermediate declarative representative, and thereafter converted to an imperative language representation of the original queries for execution. Alternatively, the queries may be directly converted to an imperative language representation of the declarative language and the imperative language queries executed on the database.

The method, system, and program product carry out SQL commands in a way that can be described by analogy to an Abstract Syntax Tree. For example, SELECT, DELETE, FETCH, ORDER BY, and the like would be at the apexes of trees, and the FROM and WHERE delimiters would be at the leaves of the tree.

The program product may reside on one computer or on several computers or on a distribution server or a disk or disks or tapes. The program itself may be encrypted and/or compressed, as would be the case o distribution media or a distribution server, for example, before installation or it may be installed on the one or more computers.

THE FIGURES

Various aspects of our invention are illustrated in the FIGURES.

DEFINITIONS

"SQL" is Structured Query Language, used for operating on Relational Data Bases in Relational Data Base Management Systems (RDBMS).

A "Declarative Language," also called an "Applicative Language" and a "Functional Language," is a computer programming language that is written in the form of function calls, where the "program" is a series of function definitions and function calls. In "Declarative" programming the model of computation is based on a system where relationships are specified directly in terms of the input data. The program is made up of sets of definitions or equations describing relations which specify what is to be computed rather than how it is to be computed. Declarative Language is characterized by non-destructive assignment of variables, and explicit representations for the data structures used. Because of the absence of "side effects" the order of execution does not matter. Historically, and as used herein, "Declarative Languages" include those derived from Lambda calculus, as well as those derived from first order logic (predicate logic).

An "Imperative Language" is language that presents a program as a series or sequence of commands. In an "Imperative" language, the model of execution is a step by step sequence of commands, with the program explicitly stating how the result is to be obtained, and where the order of execution is crucial. "Imperative" languages are further characterized by destructive assignment of variables where data structures are changed by successive destructive assignments. Historically, and as used herein, "Imperative" languages are those derived from the von Neumann model of store, an arithmetic logic unit, data, and instructions.

To be noted is that an "object oriented" language is one where the program includes a set of interacting objects. While the object paradigm may be used with both "Imperative" languages and "Declarative" languages, most implementations of object orientation are in "imperative" languages, such as SmallTalk, C++, Java, Modula2, and the like, and when "Imperative" languages are referred to herein, object oriented imperative languages are included unless clearly excluded.

DETAILED DESCRIPTION OF THE INVENTION

This invention has been motivated by the need to implement an SQL interpreter for small-footprint database management system, exemplified by IBM's DB2 Everyplace ("DB2E"). The runtime environment for DB2E is characterized by extremely tight random access memory availability and relatively weak processing power (e.g., palm-sized PDAs, embedded devices).

Pervasive computing systems, such as DB2E are illustrated in FIGS. 1 and 2. FIG. 1 illustrates the pervasive computing environment of the invention, where content, 11, illustrated in the FIGURE as relational data, collaborative data, e-mail, address book data, to-do list, memos, work flow information, database updates, software downloads, and user backup and recover are resident on one or more servers. The one or more servers are connected through connectivity services, 13, such as the World Wide Web, wireless services, and the like, to various clients. These clients include personal computers, 15, mobile computers, 17, and hand held devices, 19, among others.

FIG. 2 illustrates another aspect of the pervasive computing environment of the invention. As shown in FIG. 2, a handheld device, 18, is connected through connection services, 13, and a series of servers to databases, 12a and 12b. The servers include synchronization servers, 11a, application servers, 11b, and data servers, 11c.

Despite of this restricted computing environment, the database management system described herein is able to implement relational database management system (RDMBS) services on these devices. This is accomplished through the use of the functional programming paradigm.

The functional programming paradigm applied to query languages is described in Torsten Grust, one of the inventors herein, *Comprehending Queries*, (Ph.D. dissertation, Konstanz University, 1999) and Torsten Grust and Marc Scholl, *How To Comprehend Queries Functionally*, Journal of Intelligent Information Systems, Volume 12, pp. 191-218 (1999). The concept of comprehending queries through functional programming extends the structural recursion capabilities of functional language programming through monad comprehension to provide (1) a calculus style declarative or functional language (e.g., a lambda calculus style language) that is particularly useful during the optimization of nested queries, with (2) combinators (abstractions of the original SQL or SQL-type query operators implemented by the underlying target query engine). Grust, and Grust and Scholl describe compiling or translating or converting the query language (here, SQL) into a functional language (as a subset of LISP or a subset of HASKELL) as the intermediate language for compilation for subsequent application to the database.

However, this is not a trivial matter of a direct mapping of commands from a query language to a functional programming language, and compilation of the now functional language code to assembler and machine language. For example, functional programming languages frequently contain many commands and constructs and rules that are not needed in a sub-set of the functional programming language that is useful for implementing queries. Similarly, many of the compilers used for compiling functional languages are large and carry support for functions and code (for example, certain optimization techniques, addressing modes, control statements, etc.) that are also not needed in the sub-set of the functional programming language that is useful for implementing queries.

To this end we have created a query compiler, and an intermediate query language hierarchy between the query language (SQL) and the query engine that uses functional language (declarative language) programming constructs.

The method, system, and program product of the invention enables a small footprint DBMS to offer a flexible SQL query interface for restricted runtime environments. The techniques embodied in this invention enable these runtime environments to efficiently interpret and evaluate programs in any language and especially functional languages. As noted above in the Definitions, functional languages are languages whose programs are evaluated by the application of functions only. More particularly, functional languages are based on the concept that functions are data, just like symbols and lists are data, and that functions as data can be passed to or from other functions as data. Thus, in a functional language, a function can take another function (and not just the result of that other function) as input and apply it to data, e.g., a list, in various ways. Exemplary functional languages are ML (including Standard ML and O'Caml, by way of exemplification and not limitation), LISP and HASKELL. Applying the method, system, and program product of this invention, through ML, LISP and/or HASKELL or the like, or through functional programming paradigms, SQL queries may be constructed from functional language type functions, used as functional languages, and treated as a functional language.

The interpreter embodied in this invention draws its generality and compactness by reducing the languages it interprets to a single concept: function application. Programs (e.g., SQL queries) are completely represented as a nested composition of functions. The uniqueness and main advantage of this approach lies in the rigid enforcement of the function application idea: any language concept, including literals, variables, arithmetic, control structures, streams, and iterators, are viewed as functions and can thus be treated and evaluated in exactly the same manner.

However, direct functional language processing of query language commands and constructs for use in a small footprint environment is not yet feasible because of the "overhead" associated with rich functional languages. For example, while functional programming languages frequently contain many commands and constructs and rules that are not needed for implementing queries, those elements of the language that are needed consume a lot of memory in an environment where memory is constrained. Moreover, many of the compilers used for compiling functional languages are large and carry support for functions and code (for example, certain optimization techniques, addressing modes, control statements, etc.) that are also not needed in the sub-set of the functional programming language that is useful for implementing queries.

To this end we have created a query compiler, and an intermediate query language hierarchy between the query language (SQL) and the query engine that uses functional programming constructs and paradigms expressed in imperative computer languages. Conceptual models of our query compiler and intermediate query language hierarchy, where an imperative language representation of the original explicit (FIG. 3) or implicit (FIG. 4) declarative language representation of the original SQL query are shown in FIGS. 3 and 4.

While we speak of "compiling" or "translating," query language, directly or indirectly, explicitly or implicitly, from the query language to the imperative language representation of the declarative language form of the query, it is to be understood that this function may be implemented by pointers or look-up tables linking query language queries to imperative language representations of the declarative language representations of the query. That is, in a preferred implementation of our invention, a query, as, SELECT V FROM V WHERE V (meets some filtering criteria)---------------- may be represented as

Figure 3:
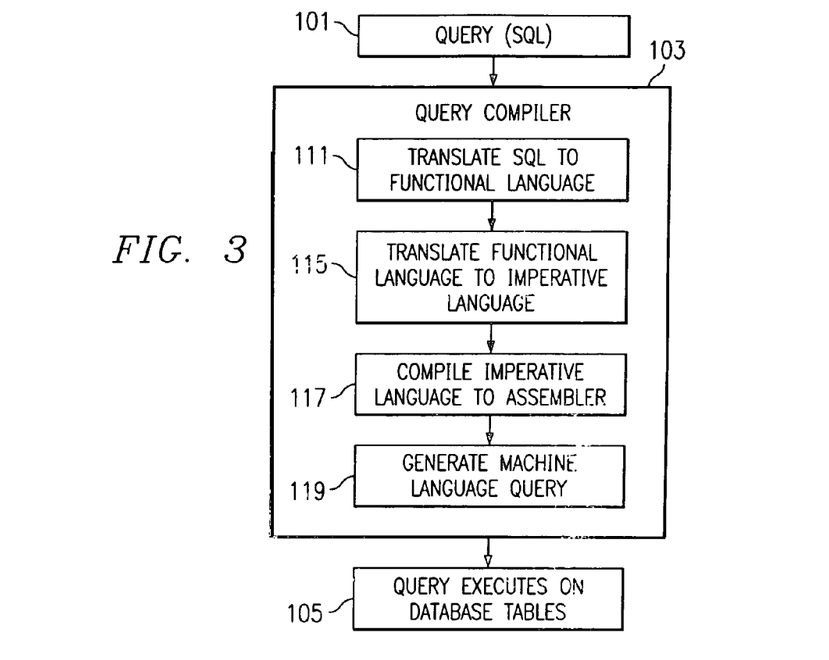
FIG. 3 illustrates a high level flow chart of one embodiment of the invention where SQL commands are first converted, translated, or compiled to a functional or declarative language, and the functional or declarative language is then translated to an imperative language, for compilation.

SELECT
   pointer to C code statement
   pointer to C code statement FROM
   pointer to C code statement
   pointer to C code statement WHERE
   pointer to C code statement
   pointer to C code statement FIG. 3 illustrates a high level flow chart of one embodiment of the invention where SQL commands are first converted, translated, or compiled to a functional or declarative language, and the functional or declarative language is then translated to an imperative language, for compilation.

Figure 4:
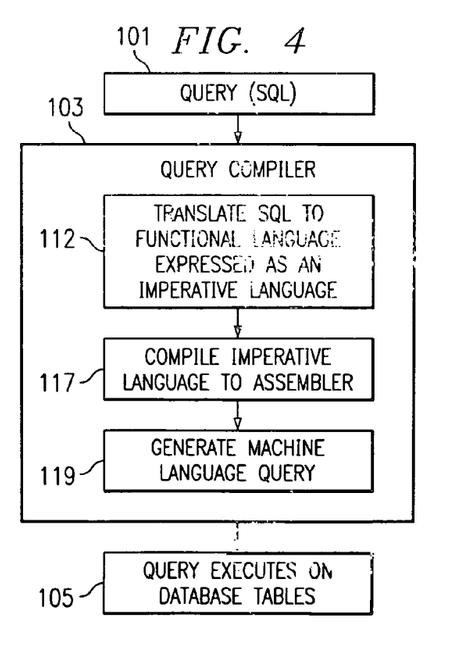
FIG. 4 illustrates a high level flow chart of an alternative embodiment of the invention where SQL commands are directly converted, translated, or compiled to an imperative language representative of the functional or declarative language representation of the SQL queries.

FIG. 4 illustrates a high level flow chart of an alternative embodiment of the invention where SQL commands are directly converted, translated, or compiled to an imperative language representative of the functional or declarative language representative of the SQL queries As shown in FIG. 3, SQL query, 101, is input to a query compiler, 103. In the query compiler, 103, the SQL query, 101, is translated or compiled, 111, to yield an intermediate representation of the query, 101, corresponding to the functional language paradigm. The intermediate representation of the query is translated or compiled, 115, to an imperative language form of the intermediate query. This imperative language form of the query, which may be an object oriented language imperative language intermediate query, is compiled, 117, in a compiler for the imperative language. This yields a low level language query, 119, which may be an assembler or actual machine language machine language query, 119, that is capable of executing on the database, 105.

Operationally, certain steps can be combined, as shown in FIG. 4. For example, the SQL query, 101, can be translated, or mapped through pointers, directly to a functional language statement expressed in an imperative language, 112. As shown in FIG. 4, SQL query, 101, is input to a query compiler, 103. In the query compiler, 103, the SQL query, 101, is translated or compiled, 112, to yield an imperative language representation of the SQL query, 101, which may be an object oriented imperative language representation of the query, 101. The imperative language, intermediate representation of the query is translated or compiled, 117, to a low level language representation of the query. This may be an assembly language representation of the original SQL query or a machine language query, that is capable of executing on the database, 105.

Figure 5:
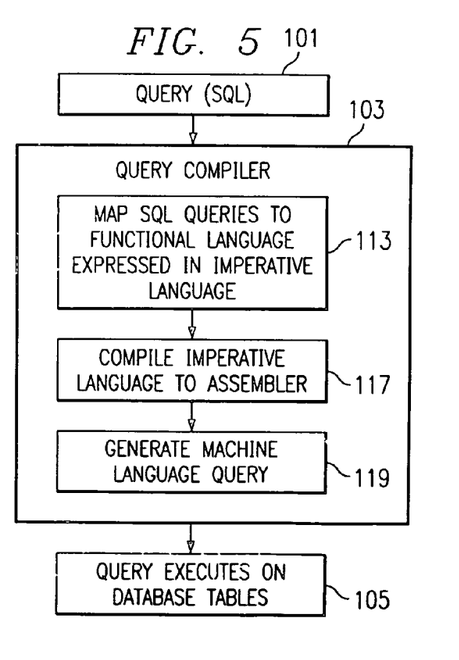
FIG. 5 illustrates a high level flow chart of an alternative embodiment of the invention where SQL commands are mapped through pointers to imperative language code to an imperative language representation of the functional or declarative language representation of the SQL queries.

Operationally, certain steps can be combined, as shown in FIG. 5 where the SQL query, 101, is mapped, e.g. through pointers, directly to a functional language statement expressed in an imperative language, 113. As shown in FIG. 5, SQL query, 101, is input to a query compiler, 103. In the query compiler, 103, the SQL query, 101, is translated or compiled, 113, through pointers to imperative language elements, to yield an imperative language representation of the SQL query, 101, which may be an object oriented imperative language representation of the query, 101. The imperative language, intermediate representation of the query is translated or compiled, 117, to a low level language representation of the query. This may be an assembly language representation of the original SQL query or a machine language query, that is capable of executing on the database, 105.

Consequently, the core of the interpreter implements function application as the machinery to execute query programs. The interpreter core indeed knows nothing about concept like literals, variables, arithmetic, control structures, and iterators. A query language to be interpreted is solely specified by a set of functions whose compositions can be evaluated by the interpreter core.

The SQL database management system of the invention has defined a set of functions that can implement a subset of the database query language SQL99 (including nested queries in the 'select', 'from', 'where' clauses, and correlated queries). This subset, by far, exceeds the set of SQL constructs provided by related products in the small-footprint database management system market.

(a) Interpreter Core

Function application is sufficient to express concepts and constructs commonly found in a query language, as SQL. The main idea is to implement the operation "apply" (hereafter denoted "app") as the only operation in the core of an interpreter for that query language. A query language is then defined by a set of functions whose compositions form actual queries. The interpreter operates on these function compositions without actual knowledge of the query language it interprets. This invention thus describes a generic query interpreter, not an SQL interpreter. Indeed, more advanced query languages such as ODMG's OQL, or application-oriented languages like those used to define and implement user-defined functions (UDFs) are possible language candidates.

Given that the supplied functions adhere to the convention to return the special value % when they try to indicate query abort, the interpreter's core can thus be specified by the following lines of C pseudo code:

```
app (func f, arg x) {
    y = f(x);
    if (y == %) then
        bailout;   else return y;
}
```

The function f to be executed is passed in as a parameter as is the argument x that function f will be applied to. The body of f may contain further calls to "app" thus defining a composition of functions to be called and evaluated. The return value of the outermost function (the root in the function calling tree) in such a composition defines the overall result of the query.

(b) Functional Language Representation of Query Language Concepts.

The SQL operations can be built from iterative and recursive operations. A simple operation employing recursion is calculation of the factorial, n!.

(i) Factorial. In functional programming, calculation of the factorial, n!, is illustrative.

In Haskell, the factorial is given by:

fac 0=1 fac n=n*fac (n−1)

and, more correctly (to prevent looping to calculate the factorial of a negative number), fac 0=1 fac n|n>0=n*fac (n−1)

or, equivalently, $$fac\ n | n == 0 = 1$$
$$| n > 0 = n * fac(n-1)$$

This is the corresponding factorial function in Common Lisp:

```
(defun fact (n)
    (cond ((zerop n) 1)
          (t (* n (fact (−n 1 )))))
``` where defun defines a function.

(ii) Recursion. How is recursion applied to searching in a functional programming paradigm ? The following set of operations illustrates the use of Haskell for determining membership in a set. First we test for the null case:

member (x, [ ])=false where x is the element tested for membership and [ ] is the set being searched. The second case is where we have a non-empty set whose first element is the item we are searching for:

member (x,s:ss)|x==s=true.

The last case is the recursive case, where we are searching a non-empty list, but the first element is not equal to the element being searched for. This is accomplished by calling the member function recursively to ask if x matches some member of the set, that is:

member (x,s:ss)|otherwise=member (x,ss)

Or, combining these statements, that is:

$$member(x, [\ ]) = false$$
$$member(x, s:ss)|x == s = true$$
$$|otherwise = member(x, ss)$$

Recursion in Common Lisp is implemented as follows:

```
(defun count-items (set)
    (cond ((null set) 0)
          (t (+1 count-items (rest set))))))
```

(iii) Iteration.

In Common Lisp, the general case of iteration is implemented using the do operator. Do enables the developer or user to specify the code that is to be executed repeatedly, the condition upon which the iteration is to be terminated, the value to be returned upon termination, any new variables (indices or do variables) to be used for the duration of the iteration, initial values for the index or do variables. This is illustrated in the following Common Lisp code for performing an iteration to count the number of "Items" in a "Set",

```
(defun do -items ( )
     (do ((    (cdr )) (sum 0 (1 + sum)))
         ((atom }}) sum)))
```

The general Common Lisp do operator allows any number of forms to be evaluated each time through the do loop, for example,

```
(defun do - items ( )
     (do ((    (sum 0)0
          (atom    ) sum)
          (setq    (cdr   ))
          (setq sum (1 + sum ))))
```

The Common Lisp and the Haskell iteration forms can be used to build SQL functions that iterate down a set of rows (files), operating on each row (file) to perform operations on selected rows (columns or cells).

(iv) Union and Intersection. Going further, functions union and intersection are inductively created. For example, union is created by $$\text{union}(s, [\ ]) \qquad s(\text{base case})$$

$$\text{union}(s, t:ts)|\text{member}(t, s) = \text{union}(s, ts)$$

(first recursive case, ignore duplicates)

$$|\text{otherwise} = t : \text{union}(s, ts)$$

(second recursive case)

Intersection is created by $$\text{intersect}(s, [\ ]) \qquad = [\ ]$$

$$\text{intersect}(s, t:ts) \quad |\text{member}(t.s) = t : \text{intersect}(s, ts)$$

$$|\text{otherwise} = \text{intersect}(s, ts)$$

(v) Filtering. A further aspect of SQL is a filtering function. Filtering is traversing a list or other enumeration picking out all elements which satisfy a particular property. In functional languages, such as Haskell, filtering is represented by a function which yields True or False depending upon whether or not the sought after property is present. Consider the very simple case of traversing a list a list of numbers to pick out the negative numbers. This is represented by     filter negative [4, −1, −10, 1, 8, 0]
    where negative x=x<0 to yield [−1, −10]

The filter function is applied to each member of a list or other enumeration to determine if that member should become part of a new list. That is:

$$\text{filter } pred[\ ] = [\ ]$$

$$\text{filter } pred(h:t)|pred\ h = h : \text{rest}$$

$$|\text{otherwise} = \text{rest}$$

$$\text{where rest} = pred\ t$$

Of course, the same strategy can be used to filter out elements, that is:

remove p=filter (not.p)

or $$\text{remove } p[\ ] = [\ ]$$

$$\text{remove } p[h:t]|ph = \text{rest})$$

$$|\text{otherwise} = h : \text{rest}$$

$$\text{where rest} = \text{remove } pt$$

A further construct useful to implement SQL operations is the simultaneous use of filter and remove to get two lists returned. In this case, one list is a list of elements with a certain property, and the other is a list of elements without the property. This is the partition function $$\text{partition } p[\ ] = [\ ]$$

$$\text{partition } p[h:t]|ph = (h : \text{yeses}, h : nos)$$

$$|\text{otherwise} = (\text{yeses}, h : nos)$$

$$\text{where}(\text{yeses}, nos) = \text{partition } pt$$

(vi) Literals. A literal (constant value) c can be represented by the constant function 'lit' below. The constant value c is returned in all cases.

lit ( ) {return c;}

(vii) Variables. Access to a variable, represented by its de Bruijn index, i, is implemented by function 'var' using a lookup in heap memory associated with the query currently in execution.

```
var (arg x) {
     return heap[x];
}
```

(viii) Streams. A stream reveals its next element when evaluated, returning EOS when exhausted.
    stream ( )

```
{
     y = next( );
     if (endofstream(y))
          return EOS;
     return y;
}
```

(ix) Filters Revisited. A filter restricts a stream s by applying predicate p to the elements in s, ignoring those elements that fail to fulfill p (s and p have been associated with this function object by the query compiler).

```
filter (arg x)
{
     do
          y = app(s, x);
     while (y != EOS && !app(p, y));
     return y;
}
```

Following this principle, the method, system, and program product of the invention provides a set of functions implementing (among other constructs) filters, joins, sorting, and grouping operators.

(c) Functional Representation of a Subset of the SQL Command Set

Figure 6:
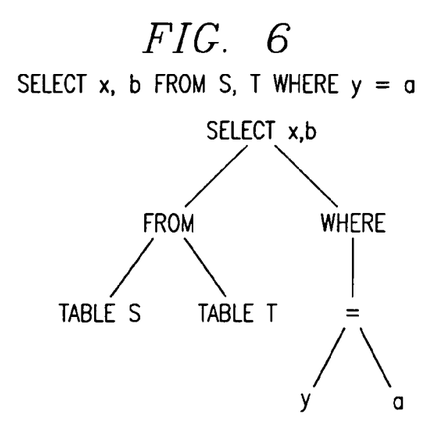
FIG. 6 is an Abstract Syntax Tree diagram of Query 1, "Select x, b from S, T, where y=a," having the C source code shown in the appendix.
Figure 7:
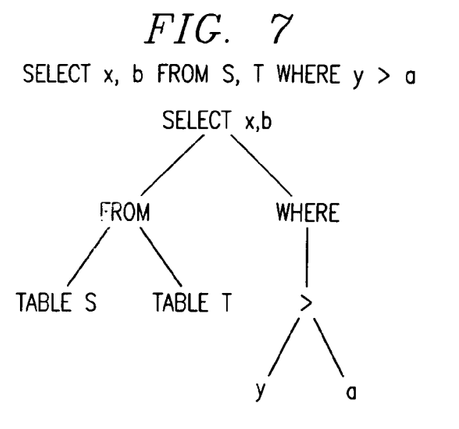
FIG. 7 is an Abstract Syntax Tree diagram of Query 2, "Select x, b from S, T, where y>a," having the C source code shown in the appendix.
Figure 8:
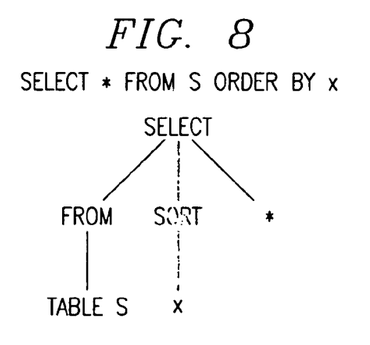
FIG. 8 is an Abstract Syntax Tree diagram of Query 3, "Select * from S, order by x," having the C source code shown in the appendix.
Figure 9:
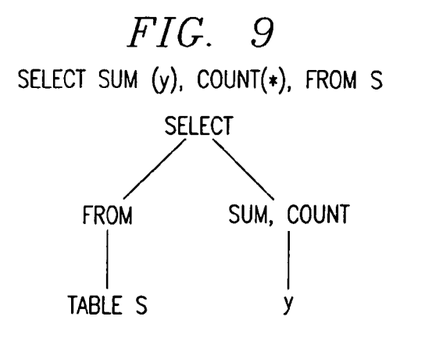
FIG. 9 is an Abstract Syntax Tree diagram of Query 4, "Select sum (y), count (*) from S," having the C source code shown in the appendix.
Figure 10:
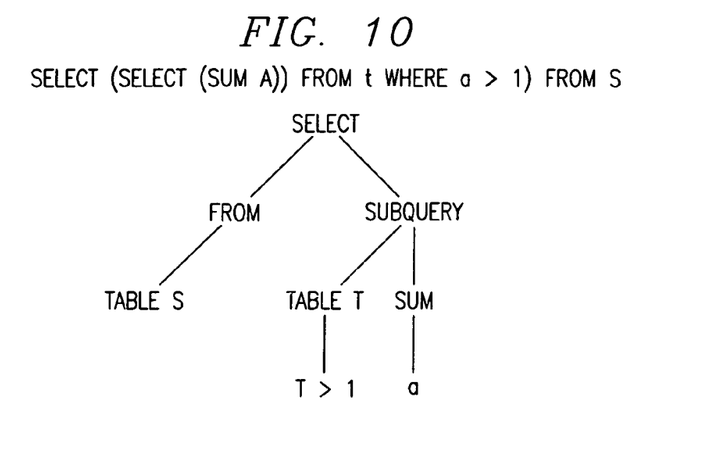
FIG. 10 is an Abstract Syntax Tree diagram of Query 5, "Select (Select (sum (a)) from T where a>1) from S," having the C source code shown in the appendix.
Figure 11:
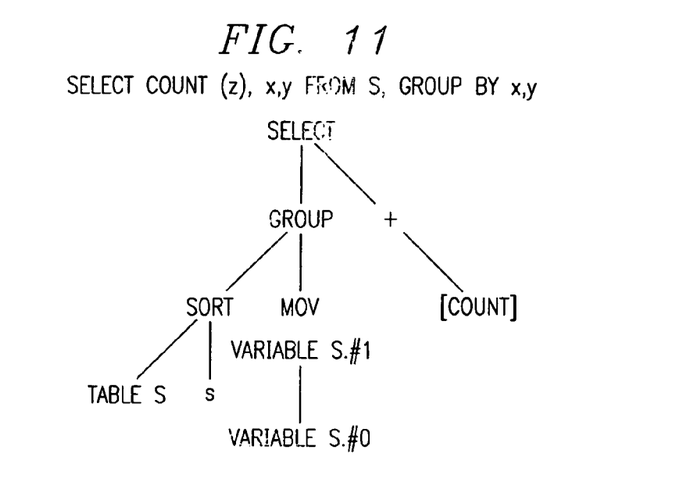
FIG. 11 is an Abstract Syntax Tree diagram of Query 6, "Select count (z), x, y from S, group by x, y," having the C source code shown in the appendix.
Figure 12:
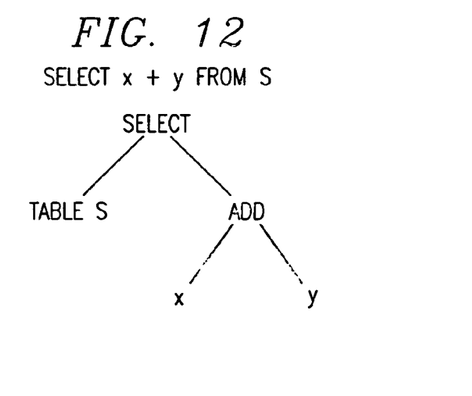
FIG. 12 is an Abstract Syntax Tree diagram of Query 7, "Select x+y from S," having the C source code shown in the appendix.
Figure 13:
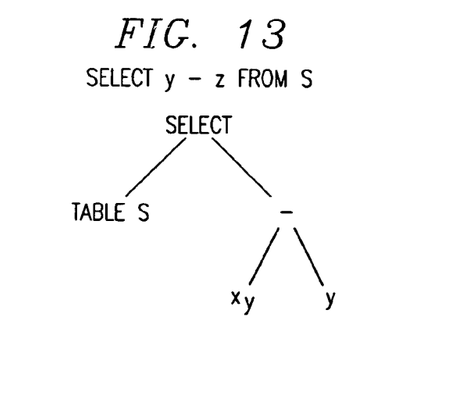
FIG. 13 is an Abstract Syntax Tree diagram of Query 1, "Select y−z from S," having the C source code shown in the appendix.

FIGS. 6 through 13 represent Abstract Syntax Tree-type diagrams of selected SQL queries, corresponding to the source code samples in Appendix A. Specifically, FIG. 6 is an Abstract Syntax Tree diagram of Query 1, "Select x, b from S, T, where y=a," having the C source code shown in the appendix. Turning to FIG. 7, FIG. 7 is an Abstract Syntax Tree diagram of Query 2, "Select x, b from S, T, where y>a," having the C source code shown in the appendix. FIG. 8 illustrates an Abstract Syntax Tree diagram of Query 3, "Select * from S, order by x," having the C source code shown in the appendix. FIG. 9 represents an Abstract Syntax Tree diagram of Query 4, "Select sum (y), count (*) from S," having the C source code shown in the appendix. FIG. 10 is an Abstract Syntax Tree diagram of Query 5, "Select (Select (sum (a)) from T where a>1) from S," having the C source code shown in the appendix. Next, FIG. 11 is an Abstract Syntax Tree diagram of Query 6, "Select count (z), x, y from S, group by x, y," having the C source code shown in the appendix. FIG. 12 is an Abstract Syntax Tree diagram of Query 7, "Select x+y from S," having the C source code shown in the appendix. Finally, FIG. 13 is an Abstract Syntax Tree diagram of Query 1, "Select y−z from S," having the C source code shown in the appendix.

To be noted is that the source code is C source code, where the imperative language code is in the form of pointers to further C code to be executed to carry out the SQL query. Also to be noted is that the pointers represent functional values, that is functions are viewed as data, in the nature of functional languages, such as ML, LISP, and HASKELL.

(d) Interpreter Details

The interpreter is designed to employ the very same function application principle during its initialization and cleanup phases, also. To achieve this, each function f is accompanied by variants f_init and f_clean which perform the necessary intialization (f_init) and garbage collection work (f_clean). Again, the interpreter core knows nothing about the actual housekeeping duties that f has to perform. The details are encapsulated in f_init and f_clean and remain opaque to the core.

The traditional approach to the construction of query interpreters treats different concepts in the underlying query language in a non-uniform manner. The different concepts normally found are the operators found in the classical relational algebra (projection, selection, join, . . . ) as well as arithmetic and relational operators (+, *, =, <, . . . ) constants, and variables.

This separation of concepts calls for a sophisticated interpreter infrastructure that honors this separation. For example, such interpreters normally include a specialized evaluation mechanism for arithmetic expressions as well as separate mechanisms to implement the stream-manipulation relational algebra operators. The resulting infrastructure tends to be complex. The need to cope with this complexity has led database vendors to significantly restrict the number of available query language constructs. Moreover, the separation of concepts results in a fixed (nested-loops based) skeleton of query execution which further restricts the set of possible SQL queries.

No such restrictions exist in the method, system, and program product described herein. As long as typing rules for function composition are obeyed, functions may be combined freely and nested to arbitrary depth to form queries of arbitrary complexity (limited only by the available stack space and heap space).

The memory footprint of the interpreter core of the invention amounts to approx. 500 bytes of machine code in a C-based implementation for palm-sized PDA's running Palm OS 3.x (running on a Motorola 68000 CPU). References to functions are implemented as C function pointers (i.e., the type 'func' used above is a function pointer type). Function app can directly invoke the referenced function by derefencing the pointer, then jumping to the resulting address. No branch table lookups or similar techniques are required. The complete SQL interpreter, i.e., its core and the accompanying set of functions defining SQL, amount to approx. 7 kB of machine code.

While the invention has been described with respect to certain preferred embodiments and exemplifications, it is not intended to limit the scope of protection thereby, but solely by the claims appended hereto.

We claim:

1. A method of managing a relational database on a pervasive computing device comprising:
   a. receiving queries on a pervasive computing device in SQL, the queries comprising a plurality of query terms;
   b. interpreting the queries on a pervasive computing device by associating at least one declarative language function with the query terms by converting the SQL to an intermediate tree representation corresponding to the declarative language function wherein the declarative language function is implemented in a declarative language that is chosen from the group consisting of ML, LISP, and HASKELL;
   c. converting the queries represented by at least one declarative language function to a plurality of JAVA statements on a pervasive computing device; and
   d. executing the JAVA statements.

2. The method of claim 1, wherein the declarative language function is identified by a reference to further code such that the declarative language function is treated as data within a plurality of JAVA statements.

3. A database management system adapted to process queries in a pervasive computing environment, said pervasive computing environment comprising at least one client adapted to interact with a server over connection services, said at least one client controlled and configured to
   a. receive the queries on a pervasive computing device in SQL, the queries comprising a plurality of query terms;
   b. interpret the queries on a pervasive computing device by associating at least one declarative language function with the query terms wherein the declarative language function is implemented in a declarative language that is chosen from the group consisting of ML, LISP, and HASKELL;
   c. convert the queries represented by the at least one declarative language function to a plurality of Java language statements on a pervasive computing device; and
   d. execute the Java language statements.

4. The system of claim 3, wherein the declarative language function is identified by a reference to further code such that the declarative language function is treated as data within the plurality of Java language statements.

5. A program product comprising computer readable program code on one or more media, said program code being capable of controlling and configuring a computer system having one or more computers to perform the process of
   a. receiving queries on a pervasive computing device in SQL, the queries comprising a plurality of query terms;
   b. interpreting the queries on a pervasive computing device by associating at least one declarative language function with the query terms wherein the declarative language function is implemented in a declarative language that is chosen from the group consisting of ML, LISP, and HASKELL;
   c. converting the queries represented by the at least one declarative language function to a plurality of Java language statements on a pervasive computing device; and
   d. executing the Java language statements.

6. The program product of claim 5, wherein the declarative language function is identified by a pointer to further code such that the declarative language function is treated as data within the plurality of Java language statements.

* * * * *